US005540235A

United States Patent [19]
Wilson

[11] Patent Number: 5,540,235
[45] Date of Patent: Jul. 30, 1996

[54] ADAPTOR FOR NEUROPHYSIOLOGICAL MONITORING WITH A PERSONAL COMPUTER

[76] Inventor: John R. Wilson, 928 N. Mapleton Ave., Oak Park, Ill. 60302

[21] Appl. No.: 268,638

[22] Filed: Jun. 30, 1994

[51] Int. Cl.$^6$ .................................. A61B 5/04; A61B 5/00
[52] U.S. Cl. .......................... 128/741; 128/731; 128/732; 128/733; 128/739
[58] Field of Search ..................................... 128/731–733, 128/739–741, 744

[56] References Cited

U.S. PATENT DOCUMENTS

| | | | |
|---|---|---|---|
| 3,880,144 | 4/1975 | Coursin et al. | 128/731 |
| 4,503,863 | 3/1985 | Katims | 128/741 |
| 4,697,598 | 10/1987 | Bernard et al. | 128/731 |
| 4,739,772 | 4/1988 | Hokanson et al. | 128/731 |
| 4,984,578 | 1/1991 | Keppel et al. | 128/732 |
| 5,195,530 | 3/1993 | Shindel | 128/731 |
| 5,195,532 | 3/1993 | Schumacher et al. | 128/739 |
| 5,381,805 | 1/1995 | Tuckett et al. | 128/741 |
| 5,405,365 | 4/1995 | Hoegnelid et al. | 128/741 |

*Primary Examiner*—Angela D. Sykes
*Assistant Examiner*—Stephen Huang
*Attorney, Agent, or Firm*—Warner J. Delaune

[57] ABSTRACT

A neurophysiological monitoring system is provided, comprising a primary module, having a first housing with a supply of electrical power from an external power source; a first detection circuit, electrically connected to the power supply, for allowing detection of analog neurophysiological signals at a predetermined site on a patient; a data processing circuit, electrically connected to the first detection circuit, for amplifying the analog signals and converting the amplified analog signals to digital signals; and an output device, electrically connected to the data processing circuit, for sending the digital signals to a personal computer for further processing; a secondary module, comprising a second housing removably connectable to the first housing, the second housing comprising a second detection circuit, electrically connectable to the data processing circuit, for allowing detection of analog neurophysiological signals at a second predetermined site on the patient; and a personal computer connected to the output device, for accepting the digital signals from the output device, for further processing and storing the digital signals, for displaying graphical information corresponding to the analog neurophysiological signals, and for controlling selected operational parameters during the monitoring. Optionally, the invention may also include a stimulation device electrically connected to the power supply, for administering a neurophysiological stimulation to the patient.

7 Claims, 14 Drawing Sheets

ADAPTOR FOR NEUROPHYSIOLOGICAL MONITORING WITH A PERSONAL COMPUTER

BACKGROUND OF THE INVENTION

I. Field of the Invention

The present invention relates generally to devices and methods used to monitor neurophysiological conditions in humans and animals, and more particularly to such devices and methods as applied to electroencepholographic (EEG), electromyographic (EMG), electrocardiographic (ECG), evoked potential (EP), and nerve conduction velocity (NCV) studies.

II. Description of Prior Art

Electromyography (EMG), electroencephalography (EEG), electrocardiography (ECG) and evoked potential (EP) measurement (collectively known as neurophysiology) have undergone rapid development in the last ten to fifteen years, requiring increasingly sophisticated machines with significant computing power and specialized controls and input devices. This has led to large devices which have become very expensive and generally immobile. Those devices which are labelled as portable are still relatively heavy, very expensive, and do not offer the computing power of their larger cousins. Fortunately, the development of personal computers, particularly laptop computers, has outpaced EMG and EEG machines, making the below-described invention possible. The latest generation of portable laptop computers has computing capability equal to or greater than most EMG and EEG machines available today. In addition, with the advent of digital signal processing, many of the specialized controls needed for running the latest machines can now be incorporated into software, so that a keyboard and mouse (or trackball) are often all that is needed to control the processes of the testing equipment. Therefore, this invention provides a solution to the problems with most of the equipment available today for such testing, namely that such equipment is bulky, expensive, complicated and sometimes difficult to obtain.

Prior to describing the preferred embodiments of the present invention, a short explanation of common neurophysiological techniques and testing is provided. Neurophysiological signals are generated by the electrical discharge of neurons in the central or peripheral nervous system or muscle fibers. The signal may occur due to voluntary or involuntary activity, or may be induced by direct stimulation from an external source. To record a neurophysiological signal, an electrode is placed at or near the nerve or muscle generating the signal (the active site), and another electrode is placed distant from the site (the inactive site). A ground electrode is also placed somewhere on the patient's body, and all three electrodes are connected to the detection instruments. The electrical discharges of nerves and muscles can be observed by changes in the voltage of the active electrode relative to the inactive electrode. To measure this effect, the signals from both the active and inactive electrodes are typically amplified and passed to a differential amplifier and/or an analog-to-digital converter, which will produce the signal corresponding to the voltage difference between the two electrodes. This signal is commonly displayed on an oscilloscope and sometimes "played" over a speaker device.

Electromyography (EMG) requires the least amount of hardware to obtain a measurable signal, because only the three electrodes described earlier are used, and no stimulating device are required. A ground electrode (G0) is placed on the skin, while the active electrode (G1) is inserted into the muscle being tested, and the inactive electrode (G2) is placed on the skin near that muscle in a monopolar array. With bipolar needles, G1 is an insulated wire travelling down a barrel which serves as G2, as is known to those of ordinary skill. The leads which connect the electrodes to the EMG machine are standardized, being either 2 mm plugs or a 6-pin DIN plug. More sophisticated EMG techniques, such as single fiber EMG or macro EMG differ in the type of needle used and the software needed to drive them. However, the inputs, preamplifiers, and analog-to-digital (A/D) converters required to process the response signals are the same.

Electroencephalography (EEG) is similar to EMG in that it records a voluntary or involuntary signal without stimulation. An array of electrodes, typically 21 in number, is placed at standardized positions on the scalp. EEG tracings are obtained by comparing the signals from one electrode with another. Most commonly, a tracing is obtained by comparing the signal from one electrode to the signal from the electrode next to it (called a "bipolar montage"). Traces may also be obtained by comparing the signals from several electrodes to a common reference electrode (called a "referential montage"). Generally, 16 traces are recorded at once, but this is limited only by the number of possible comparisons between electrodes.

For nerve conduction velocity (NCV) studies, stimulating electrodes (S1 and S2) are also required in addition to the ground (G0) and the pickup electrodes (G1 and G2). The stimulating electrodes are most commonly present on a hand-held stimulator device. An electric shock is applied over the nerve to be tested, and the signal is picked up along another segment of the nerve or is picked up at a muscle supplied by that nerve. The latency and amplitude of the signal is measured, and the process is repeated using another point of stimulation. With these multiple points of stimulation, conduction velocities can be obtained in each segment of the nerve. Some special nerve conduction tests require a specially modified reflex hammer which delivers a timing (or "triggering") signal to the receiving electronics when the operator applies the stimulus.

Evoked potential (EP) methods also require both stimulation and pickup. The arrangement of pickup electrodes varies depending on the type of EP method employed by the practitioner. However, scalp electrodes are typically placed as in an EEG test procedure. In addition, electrodes can be placed on the neck or at Erb's point (over the brachial plexus in the shoulder). The stimulus required for EP depends on the system to be tested, but can be visual (generally requiring a video display or goggles), auditory (requiring earphones or a similar auditory headset), or electrical (to stimulate sensory nerves as in nerve conduction studies). The stimulus is given repeatedly, and the signals recorded with each stimulus are averaged to reduce random background nerve activity.

The present invention is a device which may be connected to one of the input ports of a standard desktop or laptop computer, such as a serial, parallel or SCSI port. The invention contains the specialized inputs needed to record EMG and other analog neurophysiological signals. These analog signals can be digitized and processed by the laptop computer using preloaded software. The many advantages over currently available systems are readily apparent. First, such a device would dramatically lower the price of neurophysiology testing machines, because standard computer equipment is employed to control and process much of the data. Second, it will also enable manufacturers of current EMG and EEG equipment to devote greater resources to the improvement of controlling software as a complement to ongoing efforts in hardware design. Third, upgrades in hardware used for such testing will be much cheaper and easier for end users, because it would merely require the purchase of commercially available computer equipment. Fourth, the invention is highly portable because of its modular design, which is advantageous for those who wish to perform EMG and other neurophysiological tests at more than one place, or for those who perform many studies in intensive care units.

SUMMARY OF THE INVENTION

It is therefore an object of this invention to provide an adaptor for neurophysiological monitoring which directly interfaces with a personal computer.

It is also an object of this invention to provide an adaptor for neurophysiological monitoring which is lightweight, inexpensive, and easily portable.

It is a further object of this invention to provide an adaptor for neurophysiological monitoring which can be attached to additional modules for monitoring a variety of neurophysiological signals.

Yet another object of this invention is to provide an adaptor for neurophysiological monitoring which allows selective monitoring of evoked potentials, electroencephalograph information, electromyographic information, electrocardiographic information, and nerve conduction velocities.

These and other objects and advantages of the present invention will no doubt become apparent to those skilled in the art after having read the following description of the preferred embodiment which are contained in and illustrated by the various drawing figures.

Therefore, in a preferred embodiment, a neurophysiological monitoring system is provided, comprising a primary module, comprising a first housing having power means for accepting a supply of electrical power from an external power source; first detection means, electrically connected to said power means, for allowing detection of analog neurophysiological signals at a predetermined site on said patient; data processing means, electrically connected to said first detection means, for amplifying said analog signals and converting said amplified analog signals to digital signals; and output means, electrically connected to said data processing means, for sending said digital signals to personal computing means for further processing; a secondary module, comprising a second housing removably connectable to said first housing, said second housing comprising second detection means, electrically connectable to said data processing means, for allowing detection of analog neurophysiological signals at a second predetermined site on said patient; and personal computing means, connected to said output means, for accepting said digital signals from said output means, for further processing and storing said digital signals, for displaying graphical information corresponding to said analog neurophysiological signals, and for controlling selected operational parameters during said monitoring. Optionally, the invention may also include stimulation means, electrically connected to said power means, for administering a neurophysiological stimulation to said patient.

DETAILED DESCRIPTION OF THE PREFERRED EMBODIMENTS

Figure 1:
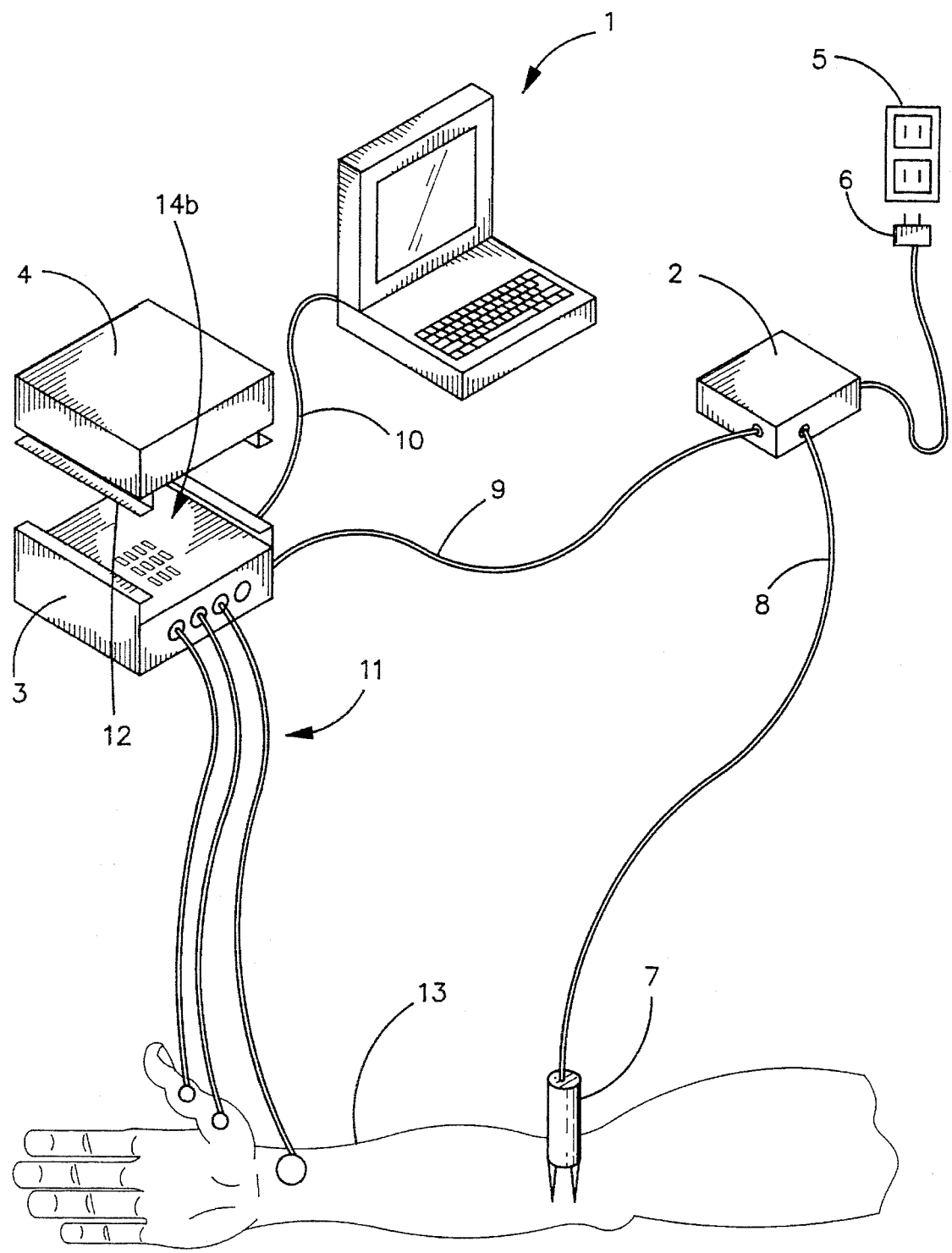
FIG. 1 is a perspective view of an overall system setup employing the modular components of the present invention.

Turning now to FIG. 1, an overall system for monitoring neurophysiological signals is shown to generally comprise a laptop or desktop computer 1, a power module 2, a primary signal conditioning module 3, and a secondary signal conditioning module 4. It will be understood that while virtually all of the electronics contained within power, primary and secondary modules 2, 3, 4 may be placed within a single housing, it is believed that important advantages may be gained from the separation of power, primary and secondary modules 2, 3, 4 as will be explained in more detail below.

Power module 2 is connected via power input socket 6 to an external source of power such as a conventional wall outlet 5. For nerve conduction velocity studies (NCV's) and evoked potential studies (EP's), stimulation means 7 is connected to power module 2 by electrical cable 8. Stimulation means 7 provides the stimulation required to elicit the required nerve or muscle response and will be explained in greater detail below. Primary module 3 is also connected to power module 2 via timing cable 9, to computer 1 via data output cable 10, and to the patient 13 by electrodes 11.

Secondary module 4 attaches to primary module 3 through locking grooves 12, or similar mechanical means, which allows electrical contacts 14a (shown best in FIG. 5) of secondary module 4 to make secure contact with corresponding electrical contacts 14b on primary module 4.

With reference to FIG. 1, during NCV's, the stimulus is triggered by the operator at stimulator 7. A timing signal is sent via cable 8 to power module 2, and via cable 9 to primary module 3. This stimulus signal triggers the beginning of signal collection, digital signal conversion by primary module 3, and data output via data cable 10 to computer 1. During EP's, when the electrodes 11 are attached to the head of patient 13, a timing signal is generated by computer 1. This timing signal travels via data cable 10 to primary module 3 where it triggers signal collection. The timing signal also travels via timing cable 9 to power module 2, where the actual stimulus signal is generated. During either NCV's or EP's, power to the primary module 3 may come from either power module 2 via timing cable 9, or from computer 1 through data output cable 10.

Figure 1A:
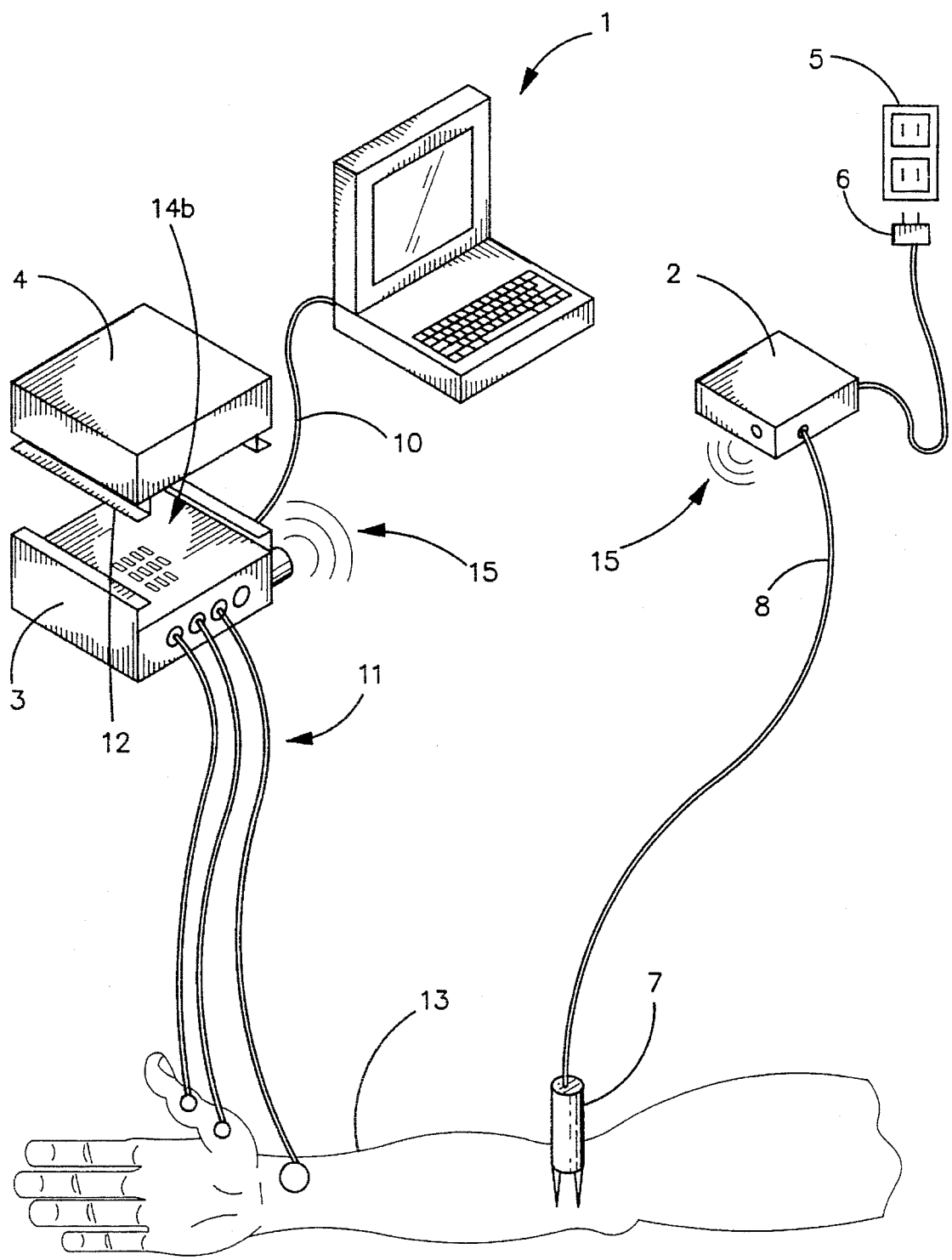
FIG. 1A is a perspective view of an alternative system setup using a wireless signalling means.

An alternate embodiment of the invention shown in FIG. 1A replaces timing cable 9 with wireless signalling means 15, such as a transmitter/receiver combination employing radio waves, infrared waves, high frequency sound waves, or other functionally equivalent electromagnetic radiation. In this embodiment, power for primary module 3 is derived from computer 1 via data cable 10. It will be understood that this arrangement offers significant advantages in small workspaces or where maximum portability is desired.

Figure 1B:
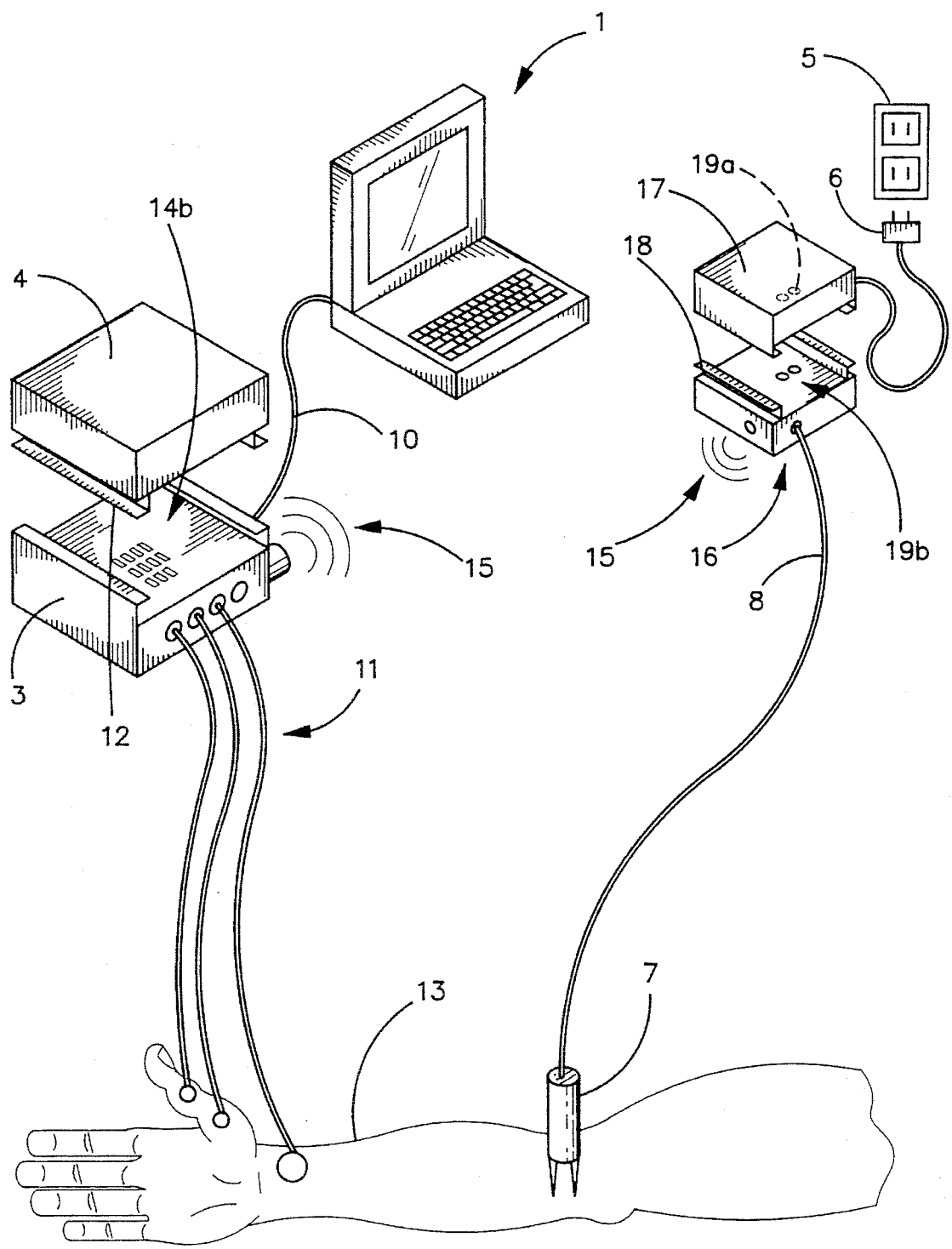
FIG. 1B is a perspective view of a further alternative system setup which employs a modified battery charger and power module for enhancing portability.

A further embodiment shown in FIG. 1B, and building upon the wireless embodiment shown in FIG. 1A, replaces power module 2 with modified power module 16 containing an internal rechargeable battery (not shown). Battery charger 17 is removably connectable to module 16 by locking grooves 18, or equivalent mechanical means, which allows secure connection between electrical contacts 19a on battery charger 17 and counterpart electrical contacts 19b on modified power module 16. Preferably, if energy storage technology permits, power module 16 should be incorporated into stimulator 7 so that stimulator can simply be recharged as needed for NCV studies and conveniently carried to the stimulation site unhindered by any power or data cables.

Figure 2:
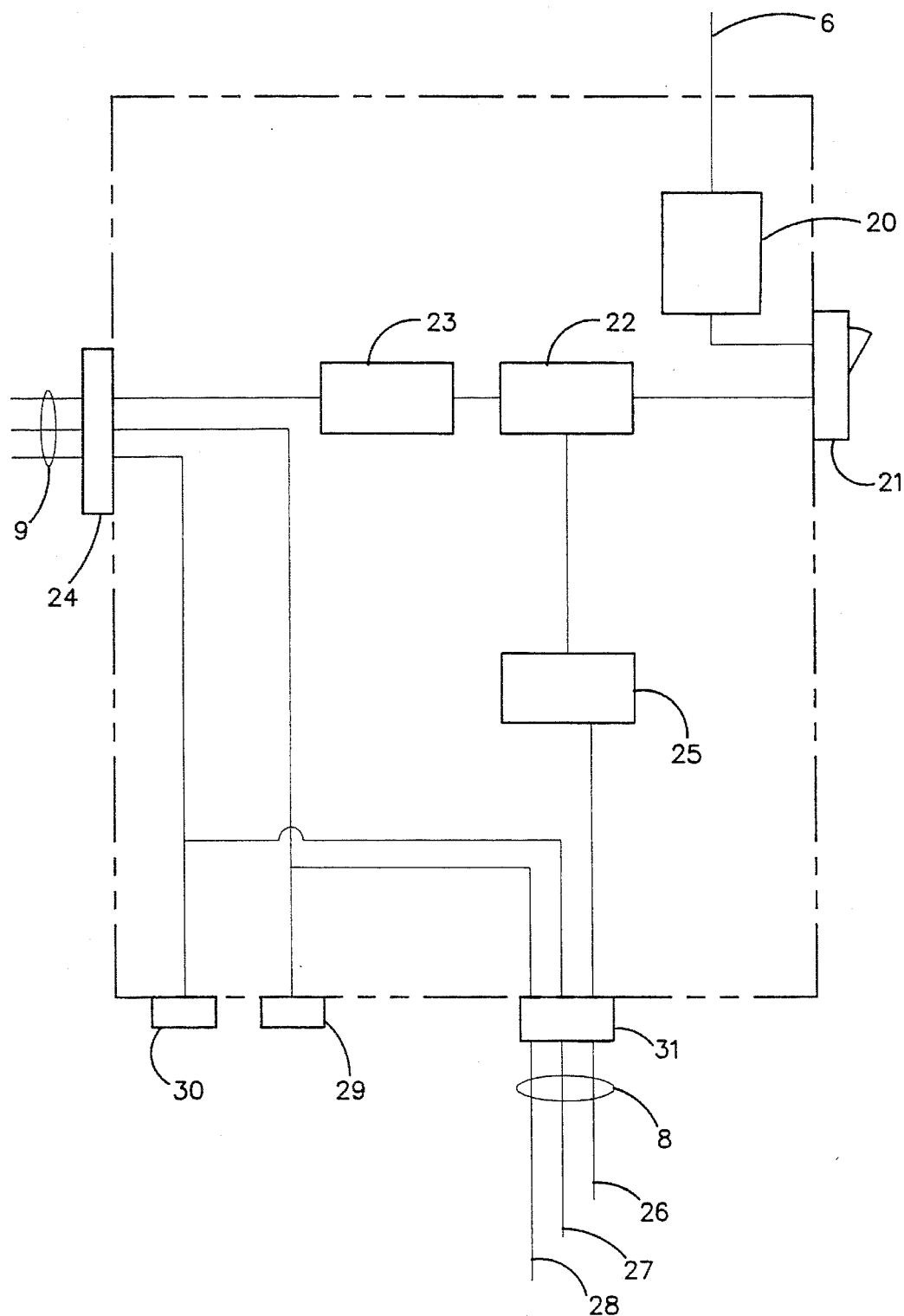
FIG. 2 is a schematic diagram of a preferred embodiment of the power module.

FIG. 2 depicts a schematic diagram of a preferred embodiment of power module 2. Power enters power module 2 via power cable 6, and surge suppression electronics 20 protect the internal components from power surges. Power switch 21 enables the user to turn off power module 2 when not in use. Current rectifier 22 converts alternating current (AC) to direct current (DC) at 120 volts DC. The DC current then flows to transformer 23, which decreases the voltage to 15 volts or some other voltage necessary or desirable to power any other components which may derive their source of power from power module 2. Current is then sent through output socket 24 and timing cable 9 to supply power to primary module 3. The 120-volt current from rectifier 22 also is transformed by transformer 25, which increases the voltage to 400 volts. This 400-volt source is for use with stimulator 7 via the stimulator output jack 31 and stimulator cable 8 through power line 26.

During NCV's and certain reflex studies, the stimulus is initiated by the operator. Thus, a timing signal is sent from stimulator 7 through stimulator jack 31 and timing line 28, through timing cable jack 24, and via timing cable 9 to primary module 3, where it triggers signal acquisition and conditioning. For reflex studies, a modified reflex hammer (not shown) is connectable to reflex hammer jack 29, through which a similar timing signal is sent to primary module 3. During EP's and some special nerve conduction tests, the stimuli must be given repetitively at a constant frequency. In these tests, a timing signal is generated by computer 1 and is sent via cable 10 to primary module 3, where it is passed on to power module 2 through timing cable 9. From the power module 2, this timing signal may be directed to either audio/video jack 30 (to which may be connected a CRT or sound generation device) or to electrical stimulator 7 by timing line 27. If directed to audio/video jack 30, the timing signal triggers a form of video patterns or audible clicks. If directed to stimulator output jack 31, the timing signal triggers a series of repetitive electric shocks through stimulator 7. In either case, the frequency and maximum number of stimuli can be set by the operator through computer 1.

Figure 2A:
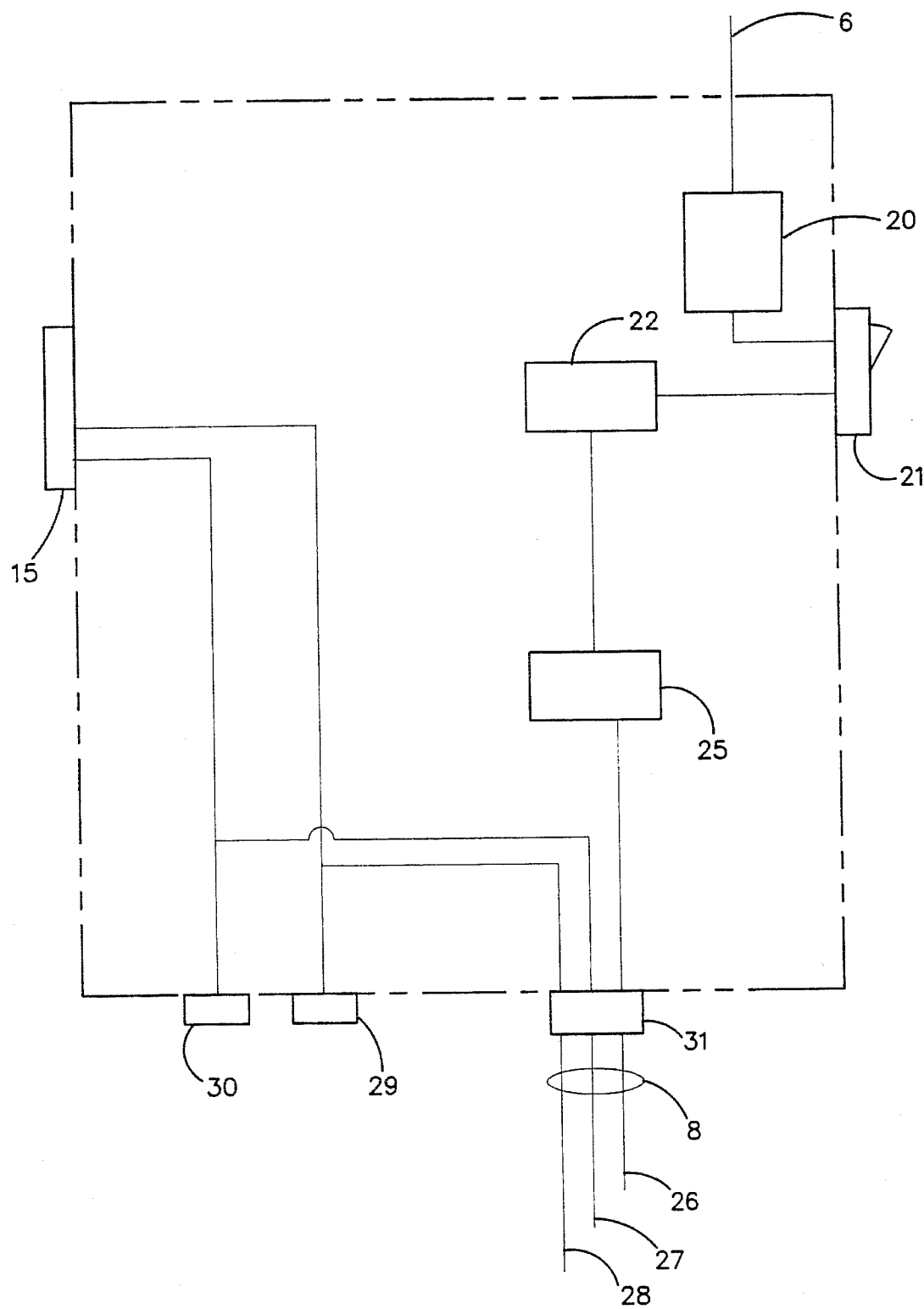
FIG. 2A is a schematic diagram of an alternative power module corresponding to the one shown in FIG. 1A.

FIG. 2A depicts in more detail the wireless embodiment mentioned in connection with FIG. 1A, where timing cable 9 is replaced with wireless signalling means 15. In this embodiment, primary module 3 and secondary module 4 must derive their power from computer 1 through data output cable 10. Wireless signalling means 15 acts as both a receiver and a transmitter of energy so that timing signals may be passed in both directions between components, depending on the study being performed and the stimulation used.

Figure 2B:
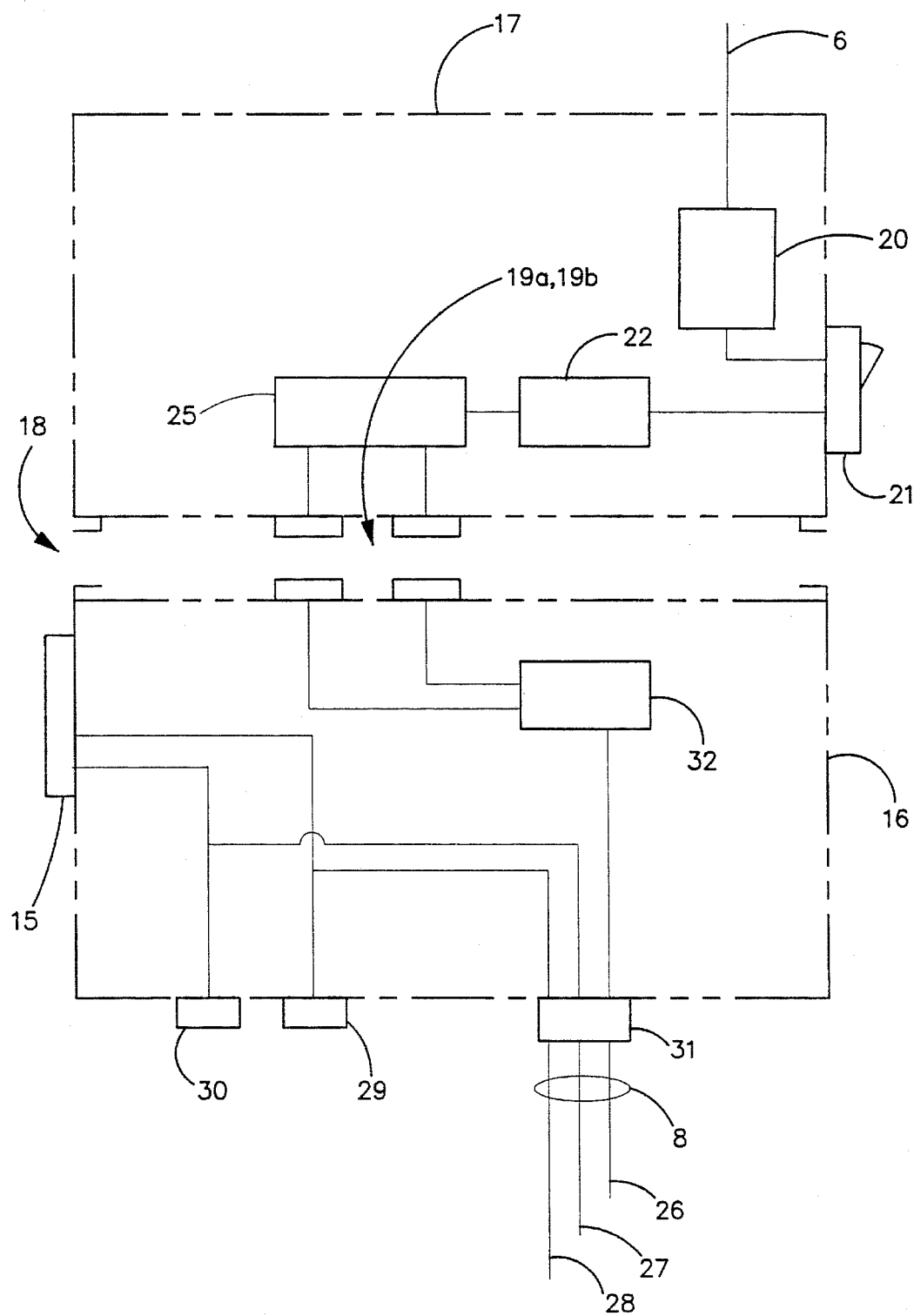
FIG. 2B is a schematic diagram of a further alternative power module corresponding to the one shown in FIG. 1B.

FIG. 2B depicts in more detail the replacement of the power module 2 with the modified power module 16 and battery charger 17 previously discussed with reference to FIG. 1B. Battery 32 is located within modified power module 16 and includes wireless signalling means 15, as well as the jacks 29, 30, 31 described earlier in FIG. 2A. However, current rectifier 22, surge suppression electronics 20, and transformer 25 are contained within battery charger 17. Electrical connections necessary to establish a charge in battery 32 are accomplished by the engagement of locking grooves 18 having complementary portions on both power module 16 and battery charger 17. When grooves 18 are engaged, electrical contacts 19a, 19b are connected, thus allowing the required flow of current.

Figure 3:
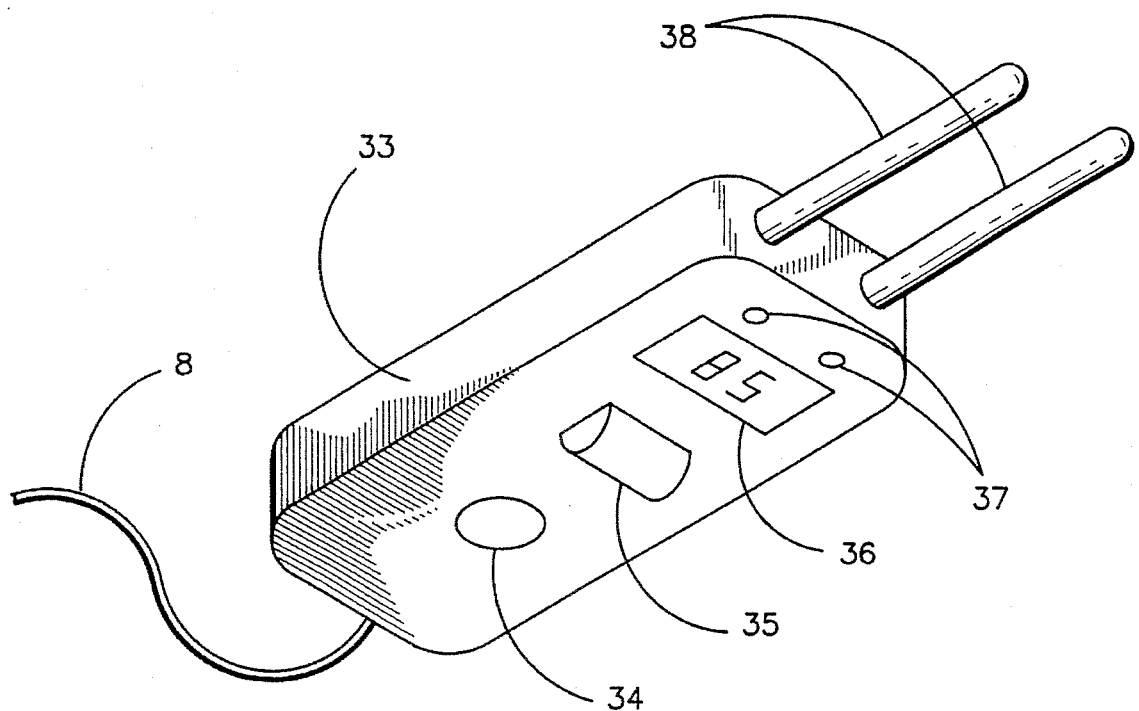
FIG. 3 is a perspective view of a preferred embodiment of the hand-held stimulator.

In FIG. 3, a preferred embodiment of the electric stimulator 7 is shown in greater detail. Stimulator 7 generally comprises a housing 33 adapted to fit easily in the human hand, a power cable 8 connected to power module 2 or modified power module 16. A pair of rigid stimulation electrodes 38 extend from the front portion of housing 33 for contacting the patient 13 and delivering the electrical stimulus. A pair of standard 2-mm sockets 37 allow the use of specialized stimulating electrodes (not shown), such as ring electrodes for fingers, needle electrodes for deep stimulation, and bar electrodes for tight areas not easily reached by housing 33. Each stimulus is delivered by pressing a trigger switch 34 with the operator's thumb. The stimulus strength is adjusted between a range of 0.0 to 100 milliamperes (mA) using a stimulus strength adjustment wheel 35. Stimulus strength indicator 36 indicates the strength of the stimulus to the operator and may comprise an LCD or LED display indicating values from 0–100 in a preferred embodiment, although any non-electronic means for indicating the stimulus strength may also be suitable.

Figure 3A:
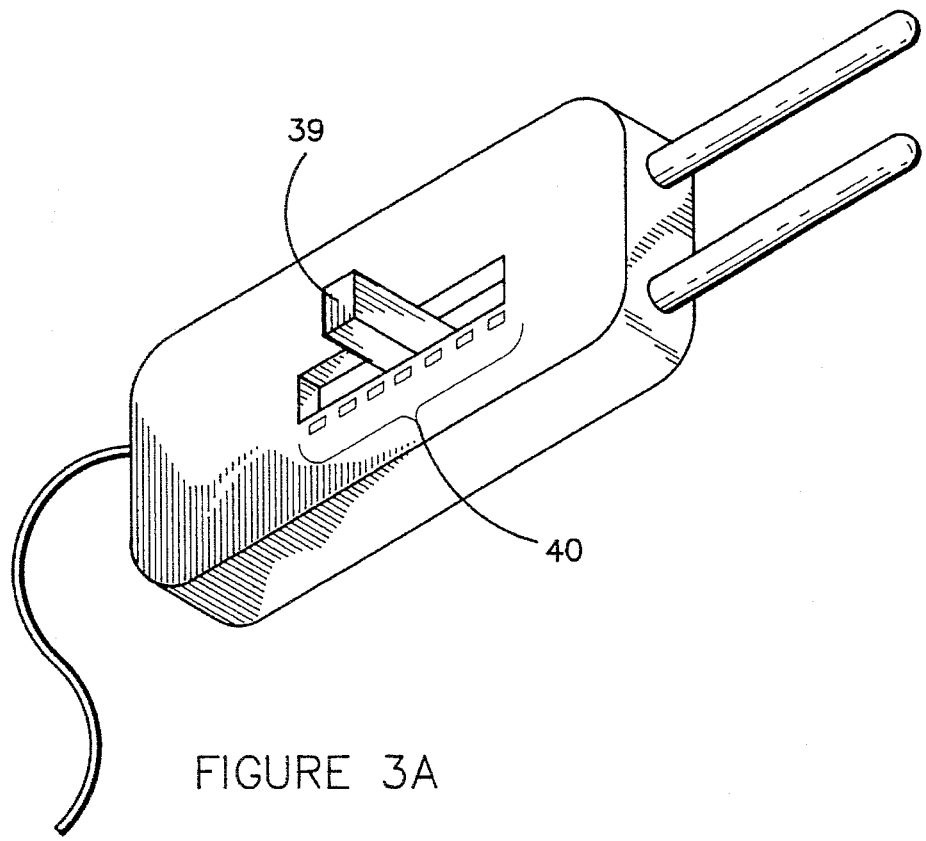
FIG. 3A is an underside view of the stimulator of FIG. 3.

FIG. 3A depicts the underside of the stimulator 7 of FIG. 3 as including a slidable stimulation duration control switch 39. In one embodiment, the duration control switch 39 is capable of seven positions corresponding to durations of 0.05, 0.1, 0.2, 0.3, 0.5, 0.75, and 1.0 milliseconds (ms), each position being labeled for visual recognition. In addition to the visual labels for these positions, each position is preferably marked by a small bump 40 or discontinuity in the housing material, thus allowing for tactile recognition of the stimulus duration. In addition to these indication methods, or perhaps as an alternative, the current duration setting may also be shown with the stimulus strength in display 36.

Figure 3B:
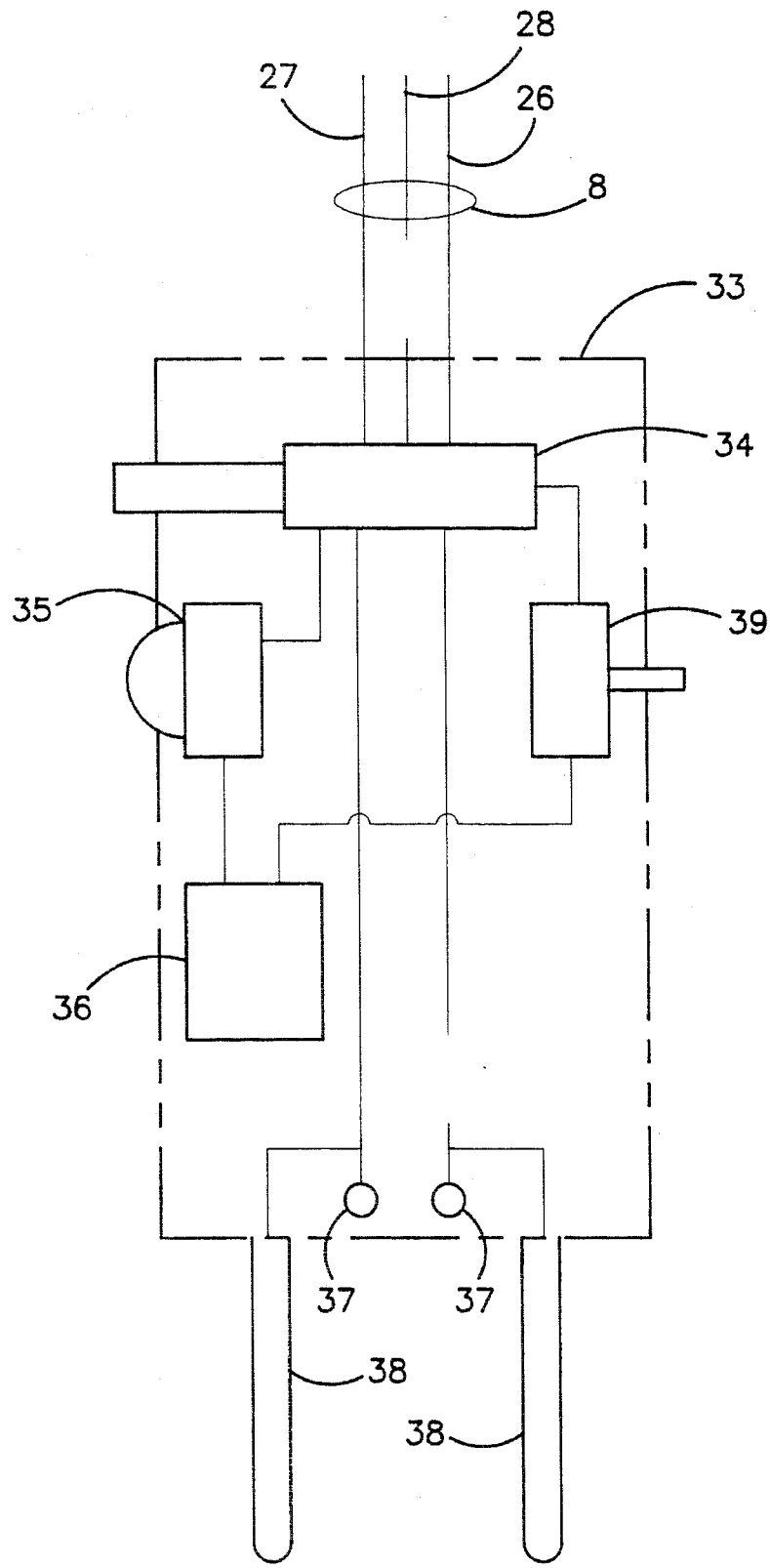
FIG. 3B is a schematic view of the stimulator shown in FIG. 3.

A schematic diagram of electrical stimulator 7 is shown in FIG. 3B. As explained elsewhere herein, power for stimulator 7 is provided by power line 26 through cable 8. The required stimulus can be delivered to electrodes 38 or alternate 2-mm jacks 37 by manual activation of switch 34 or possibly by electrical activation of switch 34 by a pre-programmed triggering signal from computer 1 through timing line 27. When a stimulus is delivered to patient 13, a timing signal is sent through timing line 28 to initiate the signal processing electronics of primary module 3. As explained earlier, the strength and duration of the stimulus is adjusted by strength regulator 35 and duration control switch 39, respectively, both of which may be displayed on display 36 for the convenience of the operator.

Figure 4:
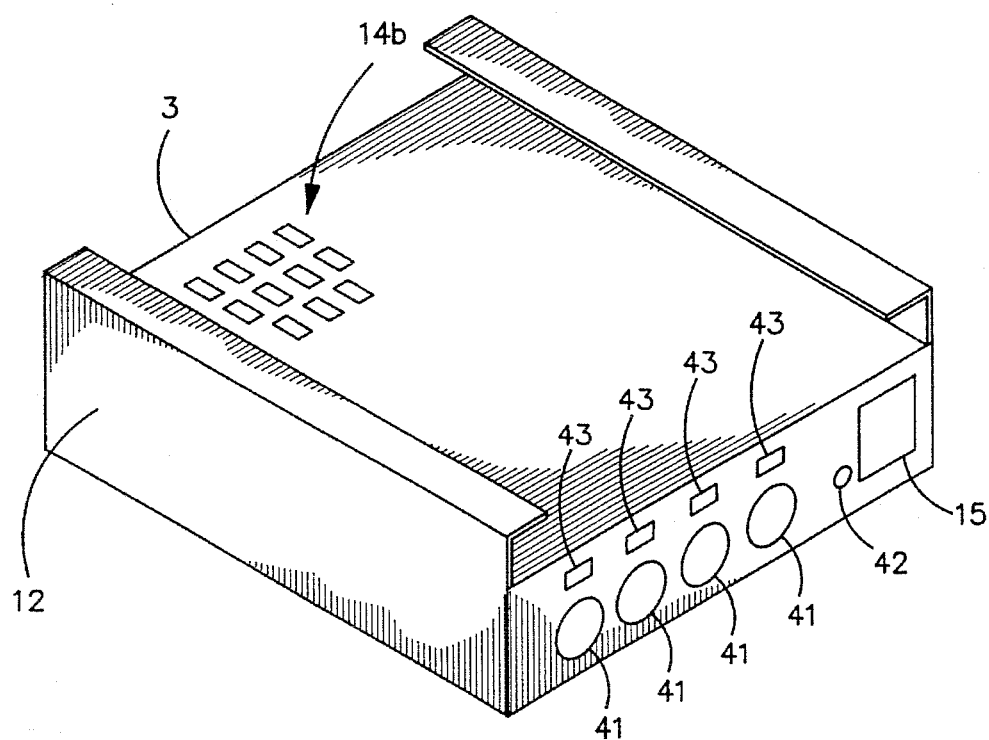
FIG. 4 is a front perspective view of a preferred embodiment of the primary module containing most of the signal conditioning electronics of the invention.
Figure 4A:
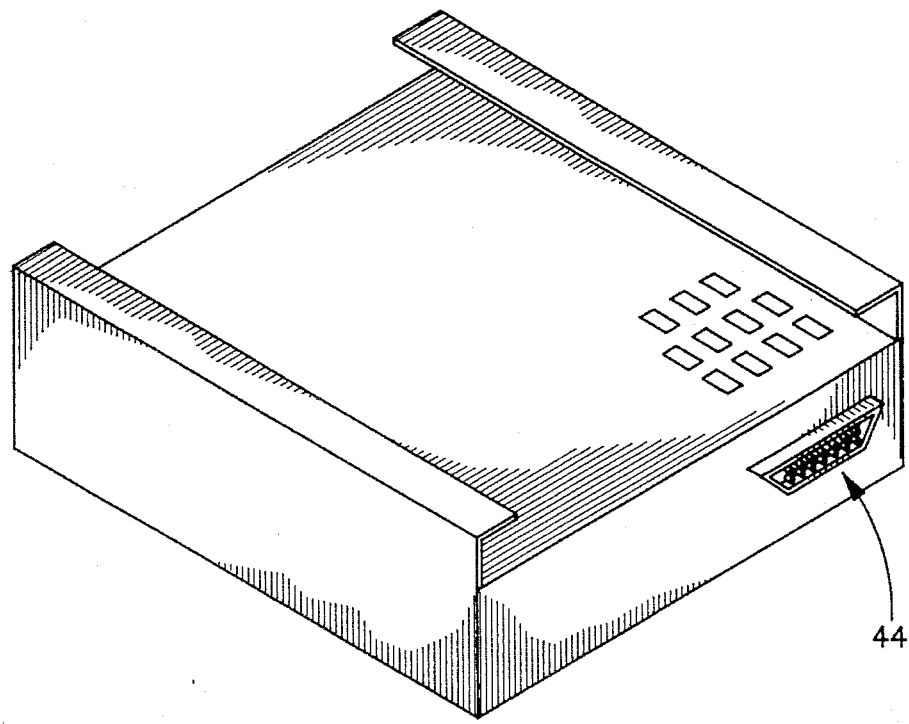
FIG. 4A is a rear perspective view of the primary module of FIG. 4.

FIG. 4 shows an external perspective view of a preferred embodiment of the 4-channel primary module 3. Primary module 3 contains virtually all of the signal processing electronics necessary for evaluating neurophysiological responses. Generally, it preferable that primary module 3 have at least two to four channels, meaning that at least two to four pairs of pickup electrodes can be used simultaneously as inputs during testing. The main inputs are four channel sockets 41 for standard DIN-6 plugs which are common in the art. These channel sockets 41 receive the unprocessed neurophysiological signals from the electrodes 11 placed on the patient 13 as shown in FIG. 1. Alternative inputs for these signals are available at contacts 14b, which also serve as contacts for connection with secondary module 4 as explained earlier. Preferably, there are a total of eleven contacts 14b, subdivided as follows: two contacts for each of the four channels of primary module 3, one contact for patient ground, and two contacts for supplying power to secondary module 4 when it is attached to primary module 3. When secondary module 4 is attached to primary module 3 by locking grooves 12, signals received by secondary module 4 are transferred to primary module 3 for further processing. Timing socket 42 for timing cable 9 is also provided, but can be overridden by wireless signalling means 15. These input/output (I/O) devices communicate with the stimulator 7 so that the delivery of the stimulus can be properly synchronized with the data collection and processing. Recall that during NCV's, the signal is generated by the stimulator and a timing signal is sent to the primary module 3, whereas in EP's and other special studies, a timing signal is generated by the computer 1 and sent to the stimulator 7 to deliver the stimulus. After signal processing, and as indicated in FIG. 4A, digitized output signals are sent to computer 1 through standard port 44 and cable 10. Other signals, such as timing signals and power from computer 1 may also be communicated through port 44, which may preferably comprise a common connection interface, such as an IEEE 488 (parallel), RS-232 (serial), or SCSI connection. Although not shown in FIG. 4, power to primary module 3 may alternatively be provided by power module 2 or modified power module 16 through a separate power receptacle (not shown) in manner known to those of ordinary skill.

Figure 4B:
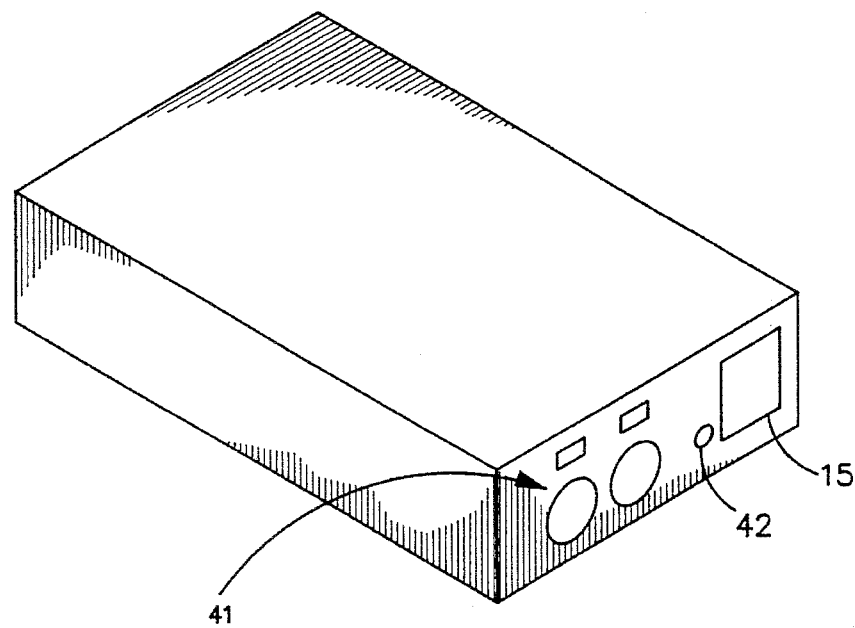
FIG. 4B is a front perspective view of an alternate embodiment of the primary module.
Figure 4C:
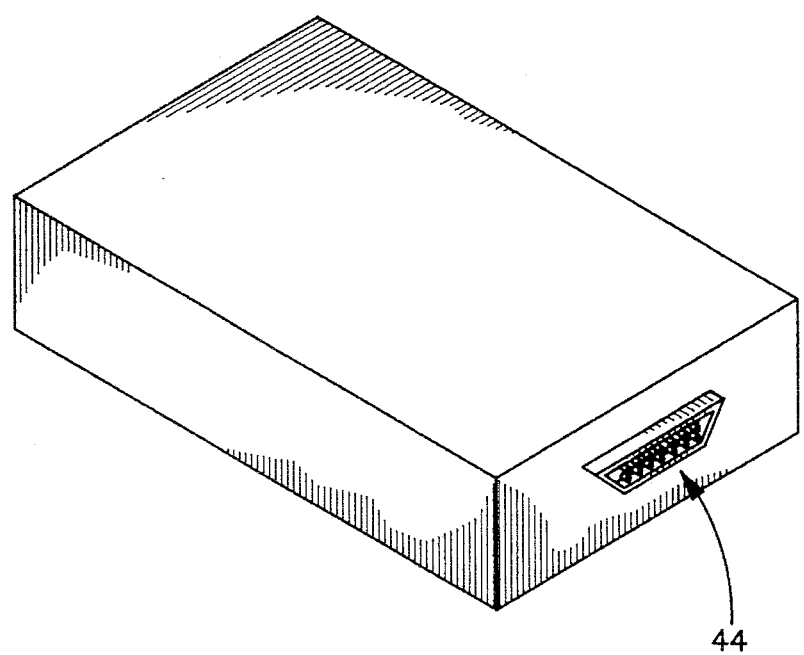
FIG. 4C is a rear perspective view of the primary module of FIG. 4B.

FIGS. 4B and 4C show an alternate embodiment of a 2-channel primary module 3 designed for use in testing environments which demand lightweight and compact construction. Because this embodiment does not allow connection with a secondary module 4, it lacks the locking grooves 12 and extra contacts 14b seen in the 4-channel version of the primary module 3. As only two channels are generally sufficient for most EMG, NCV and some EP studies, this alternative embodiment should be quite advantageous for many operators.

Figure 4D:
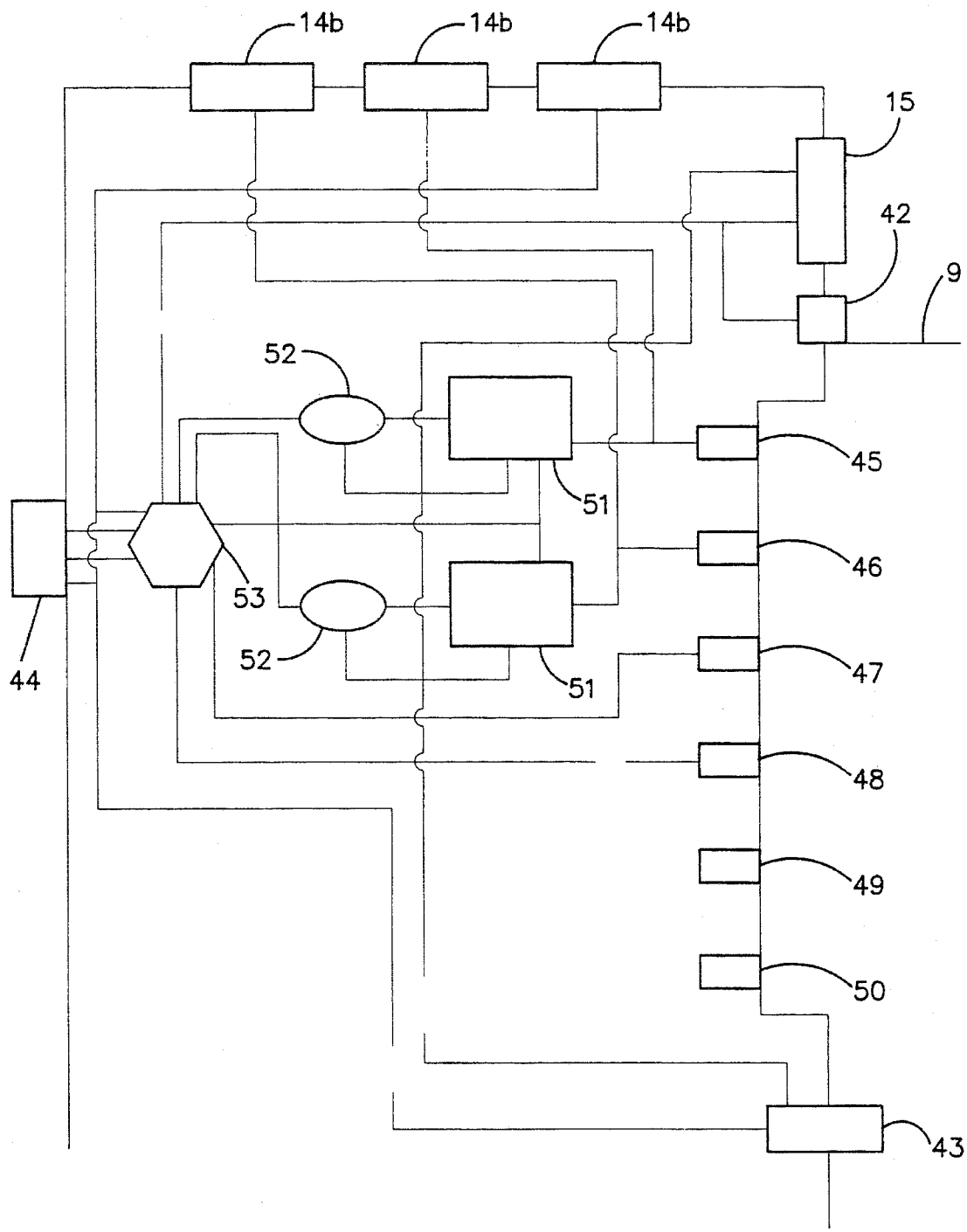
FIG. 4D is a schematic diagram of the primary module of FIG. 4 showing the electronics of a representative channel.

FIG. 4D is a schematic diagram which depicts the internal electronics of primary module 3 in the preferred embodiment of FIG. 4. Only one representative channel is depicted in the figure for the sake of simplicity, and it will be understood that any number of such channels may be included within primary module 3 when integrated in the manner described herein. All channels share a common coprocessor 53 for assimilating the digitized output and sending it through port 44 to computer 1. If power module 2 or modified power module 16 is not to be used, power is then supplied by computer 1 through port 44 to primary module 3. Although the power supply is common to all channels, each channel includes an independent on/off switch 43 so that unused channels may be selectively turned off for minimum power usage. Power to the coprocessor 53 and to the secondary module 4 through contacts 14b are supplied independently of any of the channel on/off switches 43.

Neurophysiological signals from the patient 13 enter the primary module 3 via the standard DIN-6 channel sockets 41. Signals from the active and reference electrodes enter via Pin 1 45 and Pin 2 46, respectively. Recall at this point that when secondary module 4 is attached, electrical contacts 14b transfer signals through Pins 1 and 2 45, 46, along with contacts for ground and power to secondary module 4. Signals from Pins 1 and 2 45, 46 are then amplified separately by preamplifiers 51. Preamplifiers 51 are capable of multiple gain settings which will allow the proper amplification of sensory nerve signals (0.5–50 microvolts), EMG signals (0.02–10 millivolts), and motor nerve signals (0.5–20 millivolts). These gain settings can all be adjusted through the use of controlling software between computer 1 and coprocessor 53. Once preamplified, each signal is converted by a separate analog-to-digital (A/D) converters 52. The resultant digital signals are passed to coprocessor 53, where the reference signal is subtracted from the active signal in most applications, thus acting as a differential amplifier. Under other applications, such as EEG studies, coprocessor 53 can also compare signals from different channels, rather than simply from the same channel.

With regard to the other pins of the DIN-6 socket 41, Pin 3 47 acts as the ground. All grounds are interconnected so that if one channel is grounded to the patient 13, all other channels are also grounded. Pin 4 48 may serve as the input for a thermistor (not shown), which is used to sense the temperature of the patient's skin. When the thermistor is used, the temperature signal is sent to coprocessor 53 and to computer 1, so that adjustments to final calculations can be made to reflect well-known correlations between nerve conductivity and skin temperature. Pin 4 48 is connected to all other channels, so that if a thermistor is connected, all channels will be served by it. Pins 5 and 6 49, 50 are not presently used, but can be employed in the future for additional features of the invention.

For studies which require electrical or other stimulation, the stimulus delivery and data collection are synchronized as explained previously. This is accomplished by either a hard-wired connection between primary module 3 and stimulator 7 comprising timing socket 42 and timing cable 9, or by a wireless signalling means 15 in the manner described herein. In either case, the communication of timing signals is bidirectional, so that timing signals can be generated either by computer 1 or by stimulator 7.

Figure 5A:
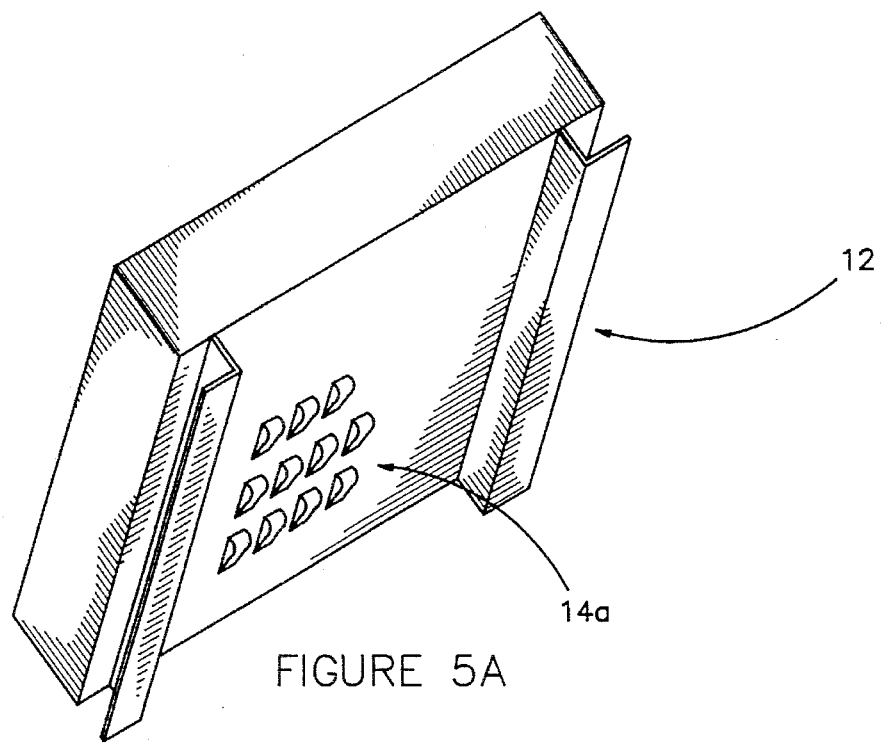
FIG. 5A is a bottom perspective view of the secondary module of FIG. 5 to show the corresponding contacts for connection to the primary module.
Figure 5:
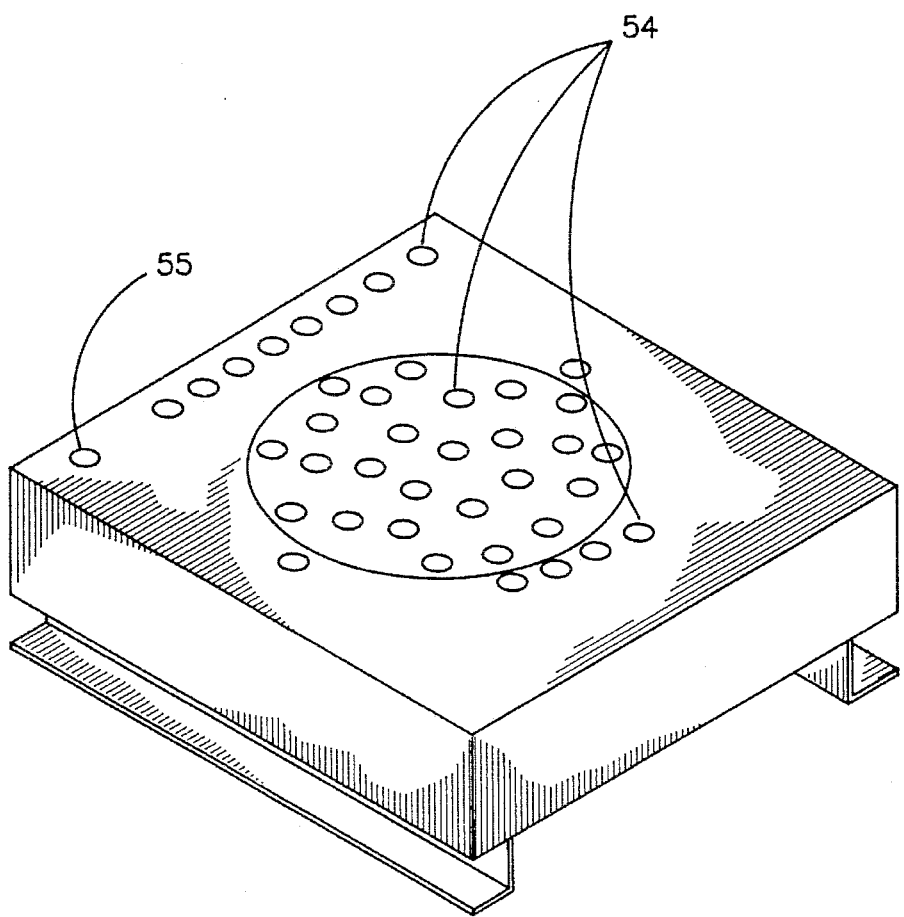
FIG. 5 is a top perspective view of the secondary module for use with EEG studies.

FIG. 5 is a top perspective view of a preferred embodiment of the secondary module 4, which is generally reserved for use with EEG studies, because it is capable of receiving analog signals from a large number of scalp electrodes. EEG electrodes are placed on the scalp of the patient 13 at standardized locations and plugged into a plurality of standard 2-mm sockets 54. Ground socket 55 is also provided for grounding the patient 13. Locking grooves 12 are matable with corresponding grooves on primary module 3 as explained earlier. When secondary module 4 is attached to primary module 3, contacts 14a on the bottom of secondary module 4 are caused to engage corresponding contacts 14a on the top of primary module 3. The engagement of contacts 14a and contacts 14b establish the needed connections for proper grounding and the transfer of electrical power and data signals between primary module 3 and secondary module 4.

Figure 5B:
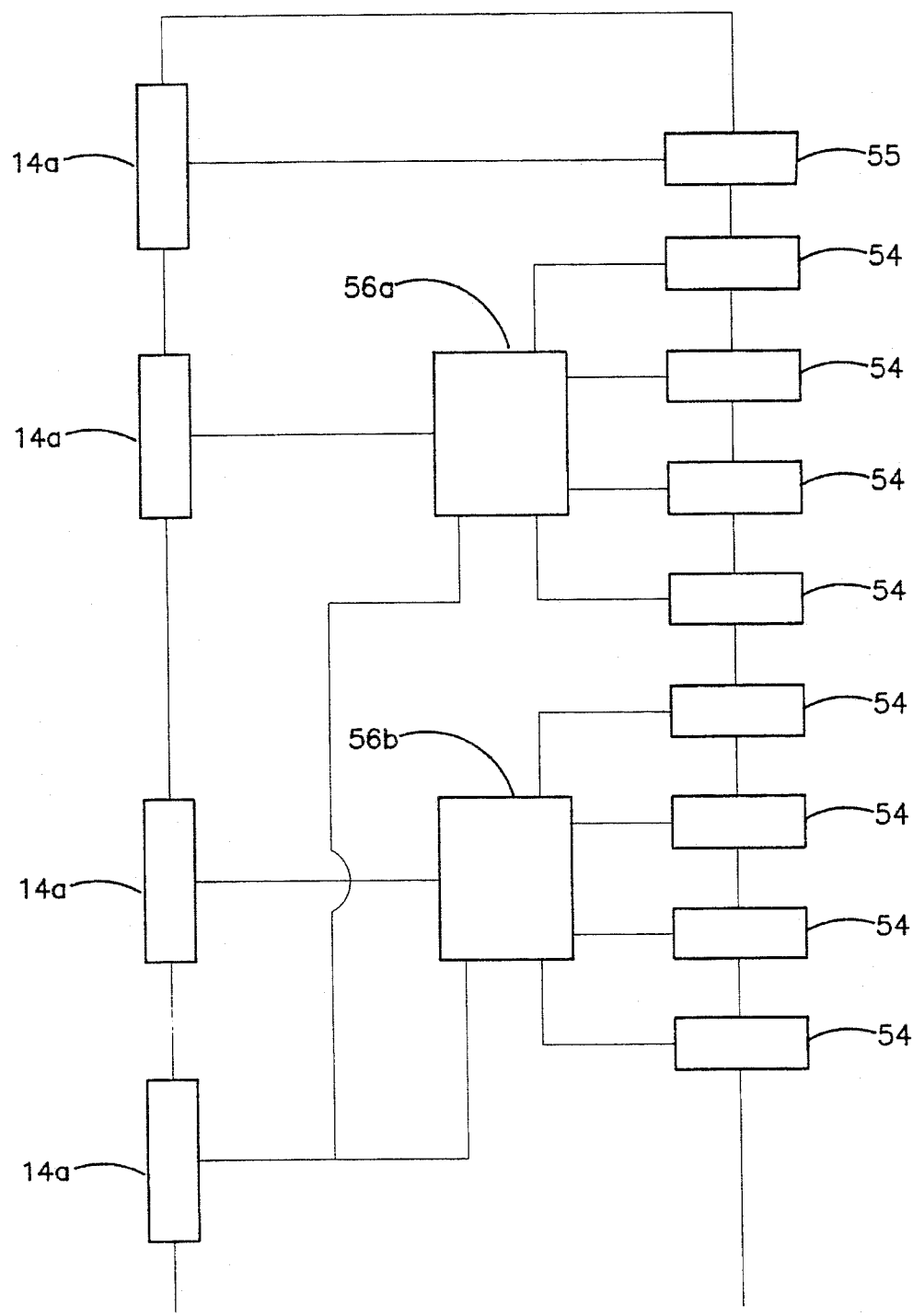
FIG. 5B is a schematic diagram of the secondary module of FIG. 5 showing the electronics of a representative channel.

FIG. 5B is an electrical schematic diagram of secondary module 4 of FIG. 5. As in the description of primary module 3, only a representative portion of secondary module 4 is shown for the sake of simplicity, although it will be understood that any number of such channels may be included within secondary module 4 when integrated in the manner described herein. In FIG. 5B, two sets of four scalp electrode input sockets 54 are shown, each set of four sockets 54 being connected to its own multiplexer unit 56a and 56b. Each multiplexer unit 56a, 56b accepts the unprocessed neurophysiological signals from four scalp electrodes and sends the signals through contact interface 14a, 14b between primary module 3 and secondary module 4. The sequential output of multiplexer unit 56a is analogous to signals entering through Pin 1 45 of the DIN-6 socket 41 on primary module 3, while the sequential output of multiplexer unit 56b is analogous to signals entering through Pin 2 46. These signals are successively preamplified and converted by primary module 3 in the manner explained elsewhere herein. Since the frequency of EEG signals is only about 0–25 Hz, each multiplexer unit 56a, 56b (and thus each channel in the primary module 3) can easily process four or input more signals without significant loss of resolution. If the 4-channel primary module 3 is employed, as many as 32 scalp electrode inputs may be used for EEG studies, although it will be understood that this number can be much higher is desired. Ground socket 55 is also connected through contacts 14a to primary module 3.

When secondary module 4 is in use, the digitized signals from the 32 scalp electrodes can be compared as needed by the appropriate data analysis software on computer 1. For example, the software would control whether the output of certain electrodes is to be compared to the output of certain other electrodes, thus enabling the operator to design his own referential or bipolar montage. The advantages gained through such use of the invention in terms of convenience, portability, and flexibility is heretofore unknown in the art of neurophysiological monitoring. It should be noted that secondary module 4 may also be used for electrocardiographic (ECG) studies as well. Instead of markings on the housing around the electrode sockets 54 indicative of the human head, a human chest may be inscribed on the housing of secondary module 4 to correspond to the actual electrode locations on the chest of patient 13. Of course, electronic operation of secondary module 4 would remain unchanged.

Although not particularly shown in the figures, an alternate embodiment of the present invention may comprise a single, unitary module that may be used for EP's, EEG's, and ECG's, as well as for NCV and EMG studies. Such an embodiment would simply involve hard-wiring the electrical connections between primary module 3 and secondary module 4 within a more compact case, thus removing the need for locking grooves 12. It can be seen that virtually all of the advantages of the invention can also be obtained through this embodiment, because personal computer 1 still acts as a replacement for expensive computing equipment and oscilloscopes designed specifically for medical applications. However, those who perform EEG's or ECG's infrequently may not wish to carry the extra weight of a unitary embodiment, and may prefer the 4-channel or the 2-channel primary module 3 as previously described herein.

Figure 6:
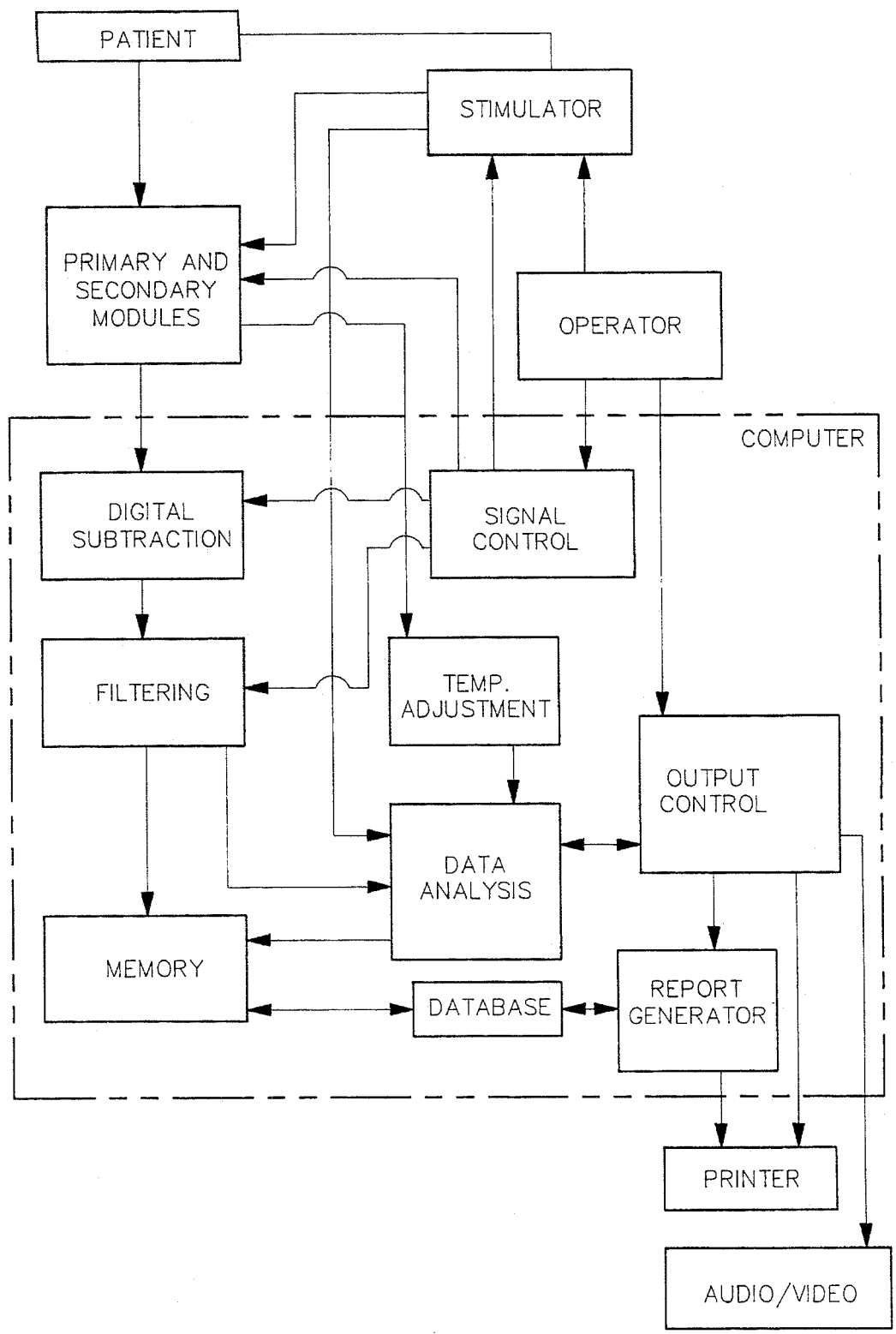
FIG. 6 is a flowchart depicting how and where neurophysiological input signals are processed and converted to the required digital output signals.

FIG. 6 is a flowchart which shows the flow of information between the major electronic components of the testing environment, namely the stimulator, computer 1, primary module 3, and secondary module 4. Also depicted is the relationship between the patient 13 and these components, a possible flowchart of processes which would occur within computer 1 during testing procedures, and the visual and auditory display of the results to the operator.

Many advantages are apparent from use of the present invention. It will lower the cost of providing neurophysiological testing by lowering the cost of the hardware required to perform such tests. The development of new hardware used for neurophysiological testing will become cheaper, as it will become standardized with the computer industry as a whole. This invention transforms a laptop computer into an easily portable neurophysiological testing unit, which is currently not available. This modular concept for neurophysiological testing, namely a secondary module 4 which has inputs for EEG feeding into a primary module 3 with preamplifiers and A/D converters, where the primary module 3 can be used separately for EMG's and EP's, is unknown to this industry, and it eliminates the need for duplicate hardware.

The 4-channel model shown in FIG. 4 allows the conversion of a desktop or laptop computer into an electrodiagnostic tool as powerful as any on the market today, because most of the computing power is contained within computer 1. Moreover, the use of computer 1 affords the operator access to highly developed graphical software currently available for such machines, rather than being limited to cryptic readouts and LED signals on other equipment. All of this is accomplished while keeping the invention lightweight enough to be easily portable. It also allows upgrading of the hardware one module at a time, which is far less expensive to the operator over time.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. An adaptor for use with a personal computer for monitoring neurophysiological conditions of a patient, comprising:

(a) a first housing having power means for accepting a supply of electrical power from an external power source;

(b) first detection means, electrically connected to said power means, for allowing detection of analog neurophysiological signals at a predetermined site on said patient;

(c) data processing means, electrically connected to said first detection means, for amplifying said analog signals and converting said amplified analog signals to digital signals;

(d) output means, electrically connected to said data processing means, for sending said digital signals to a personal computer for further processing; and (e) a second housing removably connectable to said first housing, said second housing comprising second detection means, electrically connectable to said data processing means, for allowing detection of analog neurophysiological signals at a second predetermined site on said patient.

2. The adaptor according to claim 1, wherein said second detection means comprises at least eight response electrodes adapted to receive said analog neurophysiological signals at said second predetermined site.

3. The adaptor according to claim 2, wherein said second detection means includes one or more multiplexing means for accepting and processing four or more of said analog neurophysiological signals.

4. A neurophysiological monitoring system, comprising:
  (a) a primary module, comprising:
    (i) a first housing having power means for accepting a supply of electrical power from an external power source;
    (ii) first detection means, electrically connected to said power means, for allowing detection of analog neurophysiological signals at a predetermined site on a patient;
    (iii) data processing means, electrically connected to said first detection means, for amplifying said analog signals and converting said amplified analog signals to digital signals; and
    (iv) output means, electrically connected to said data processing means, for sending said digital signals to personal computing means for further processing;
  (b) a secondary module, comprising:
    (i) a second housing removably connectable to said first housing, said second housing comprising second detection means, electrically connectable to said data processing means, for allowing detection of analog neurophysiological signals at a second predetermined site on said patient; and
  (c) personal computing means, connected to said output means, for accepting said digital signals from said output means, for further processing and storing said digital signals, for displaying graphical information corresponding to said analog neurophysiological signals, and for controlling selected operational parameters during said monitoring.

5. The neurophysiological monitoring system according to claim 4, wherein said second detection means comprises at least eight response electrodes adapted to receive said analog neurophysiological signals at said second predetermined site.

6. The adaptor according to claim 5, wherein said second detection means includes one or more multiplexing means for accepting and processing four or more of said analog neurophysiological signals.

7. The adaptor according to claim 4, wherein said first detection means comprises at least two response electrodes adapted to receive said analog neurophysiological signals from said patient at said first predetermined site.

* * * * *